United States Patent
Kim et al.

(10) Patent No.: US 12,351,864 B2
(45) Date of Patent: Jul. 8, 2025

(54) METHOD AND DEVICE FOR AMPLIFYING AND DETECTING GENE

(71) Applicant: ELECTRONICS AND TELECOMMUNICATIONS RESEARCH INSTITUTE, Daejeon (KR)

(72) Inventors: Jin Tae Kim, Daejeon (KR); Kwang Hyo Chung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1099 days.

(21) Appl. No.: 17/313,905

(22) Filed: May 6, 2021

(65) Prior Publication Data

US 2021/0388428 A1      Dec. 16, 2021

(30) Foreign Application Priority Data

Jun. 12, 2020   (KR) ................ 10-2020-0071677

(51) Int. Cl.
| | |
|---|---|
| G01N 21/64 | (2006.01) |
| B01L 7/00 | (2006.01) |
| B81B 1/00 | (2006.01) |
| C12M 1/34 | (2006.01) |
| C12Q 1/6848 | (2018.01) |

(52) U.S. Cl.
CPC .......... *C12Q 1/6848* (2013.01); *B81B 1/006* (2013.01); *G01N 21/6428* (2013.01); *B81B 2201/05* (2013.01); *B81B 2203/0338* (2013.01); *G01N 2201/0231* (2013.01)

(58) Field of Classification Search
CPC ......... C12Q 1/6848; G01N 2021/6482; G01N 21/6428; G01N 2201/0231
See application file for complete search history.

(56) References Cited

U.S. PATENT DOCUMENTS

| | | |
|---|---|---|
| 8,735,103 B2 | 5/2014 | Chung et al. |
| 10,138,513 B2 | 11/2018 | Chung et al. |
| 10,344,208 B2 | 7/2019 | Vasiliev et al. |

(Continued)

FOREIGN PATENT DOCUMENTS

| | | |
|---|---|---|
| KR | 10-2008-0052220 A | 6/2008 |
| KR | 10-2013-0086894 A | 8/2013 |

(Continued)

OTHER PUBLICATIONS

Debjani Pal et al., "A power-efficient thermocycler based on induction heating for DNA amplification by polymerase chain reaction", Review of Scientific Instruments 75, 2880, 2004.

(Continued)

*Primary Examiner* — Lydia Edwards

(57) ABSTRACT

Provided is a device for amplifying and detecting a gene. The device for amplifying and detecting the gene includes a gene amplification chip comprising channels through which a sample flows and transparent heaters provided on the gene amplification chip. The channels include a first channel, a second channel, and a third channel, and the first to third channels have a triangular loop structure, and the transparent heaters include a first transparent heater, a second transparent heater, and a third transparent heater, which are respectively provided on the first to third channels.

7 Claims, 9 Drawing Sheets

(56) References Cited

U.S. PATENT DOCUMENTS

| | | | |
|---|---|---|---|
| 2006/0280629 A1* | 12/2006 | Chang | F04F 1/06 |
| | | | 417/313 |
| 2008/0064086 A1 | 3/2008 | Lee et al. | |
| 2008/0176292 A1* | 7/2008 | Ugaz | B01L 7/525 |
| | | | 435/286.1 |
| 2009/0275117 A1 | 11/2009 | Sandell | |
| 2010/0267127 A1 | 10/2010 | Chung et al. | |
| 2014/0080133 A1* | 3/2014 | Chen | H05K 3/4644 |
| | | | 435/6.12 |
| 2020/0261858 A1 | 8/2020 | Seo et al. | |

FOREIGN PATENT DOCUMENTS

| | | |
|---|---|---|
| KR | 10-1318988 B1 | 10/2013 |
| KR | 20160027404 A | 3/2016 |
| KR | 10-2020-0005532 A | 1/2020 |

OTHER PUBLICATIONS

Geoffrey Mulberry et al., "3D printing and milling a real-time PCR device for infectious disease diagnostics", Plos One, 2017.

* cited by examiner

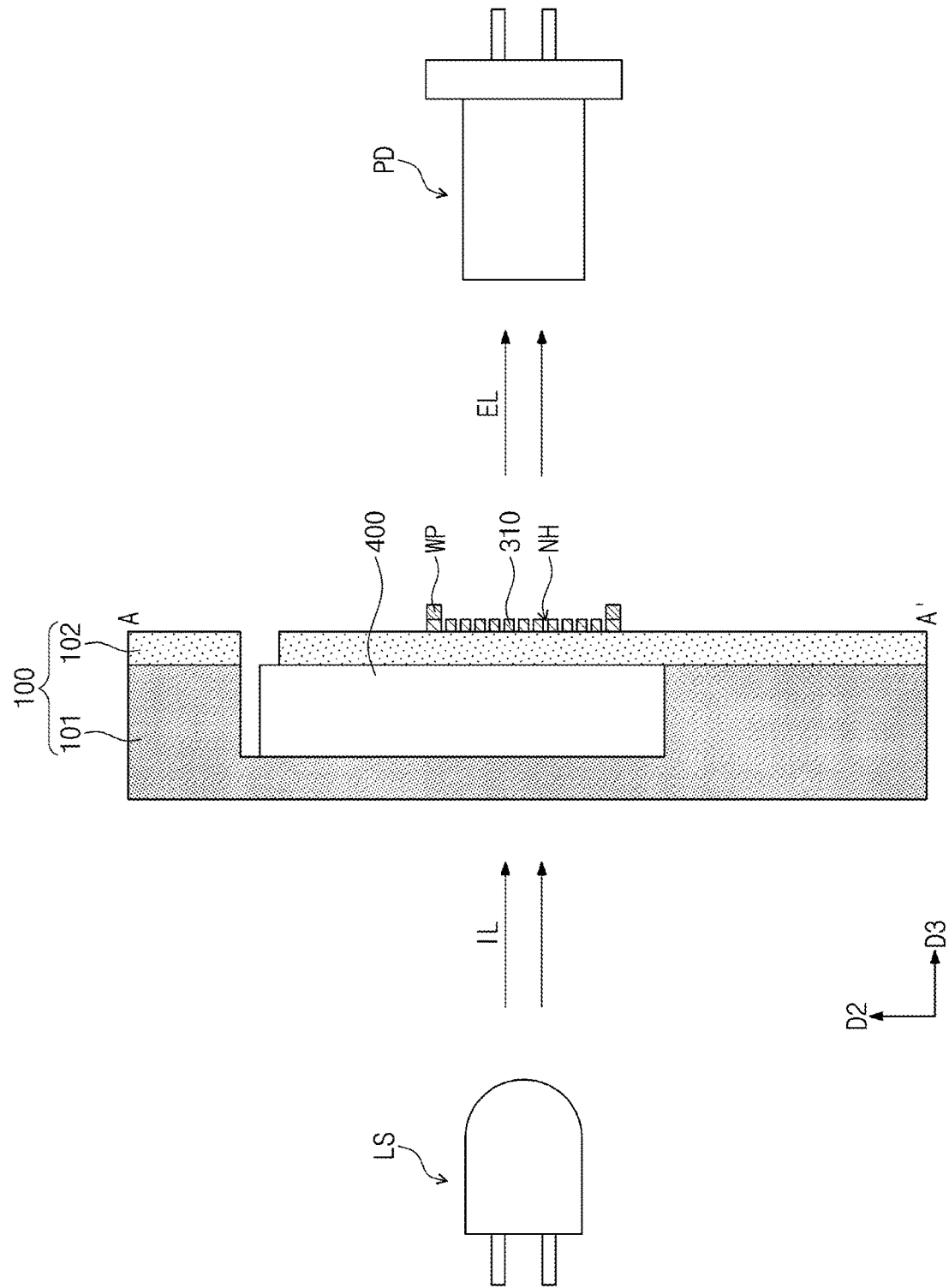

METHOD AND DEVICE FOR AMPLIFYING AND DETECTING GENE

CROSS-REFERENCE TO RELATED APPLICATIONS

This U.S. non-provisional patent application claims priority under 35 U.S.C. § 119 of Korean Patent Application No. 10-2020-0071677, filed on Jun. 12, 2020, the entire contents of which are hereby incorporated by reference.

BACKGROUND

The present disclosure herein relates to a method and device for amplifying and detecting a gene, and more particularly, to a device for amplifying and detecting a gene, which includes a transparent heater, and a method for amplifying and detecting a gene by using the same.

In general, since a small amount of genes are contained in a gene analysis object sample, an amplification process that increases in number of genes is essential. A representative technology for the gene amplification is a polymerase chain reaction (PCR) technology. In the PCR technology, processes of denaturation, annealing, and extension are sequentially and repetitively performed to amplify genes. Since each process is performed at a different temperature, the gene has to be amplified while changing a temperature of the sample.

To efficiently perform such a gene amplification process, various gene amplification devices have been developed. For example, a method using a heating block or a method in which a coil-type heater is installed around the sample are being used. However, there is a limitation that a temperature loss occurs, and a gene amplification chip has to be separated from the device for the gene analysis.

SUMMARY

The present disclosure provides a device and method for amplifying and detecting a gene, which are capable of measuring a degree of gene amplification while reducing a temperature loss and without separating a gene amplification chip.

Technical objects to be solved by the present invention are not limited to the aforementioned technical objects and unmentioned technical objects will be clearly understood by those skilled in the art from the specification and the appended claims.

An embodiment of the inventive concept provides a device for amplifying and detecting a gene includes: a gene amplification chip including channels through which a sample flows; and transparent heaters provided on the gene amplification chip, wherein the channels include a first channel, a second channel, and a third channel, and the first to third channels have a triangular loop structure, and the transparent heaters include a first transparent heater, a second transparent heater, and a third transparent heater, which are respectively provided on the first to third channels.

In an embodiment of the inventive concept, a method for amplifying and detecting a gene includes: introducing a sample into channels formed inside a gene amplification chip; heating the sample through transparent heater provided on the gene amplification chip to allow the sample to flow along the channels; providing incident light from a light source to the gene amplification chip; and measuring an intensity of emission light emitted from a fluorescent material within the sample through a photodetector, wherein the channels include a first channel, a second channel, and a third channel, which have a triangular loop structure, and the transparent heater includes a first transparent heater, a second transparent heater, and a third transparent heater, which are respectively provided on the first to third channels, wherein the first transparent heater extends along the first channel, the second transparent heater extends along the second channel, and the third transparent heater extends along the third channel.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings:

FIGS. 7 to 9 are cross-sectional views for explaining a method for measuring a degree of gene amplification by using the device for amplifying and detecting the gene according to embodiments of the inventive concept.

DETAILED DESCRIPTION

Figure 1:
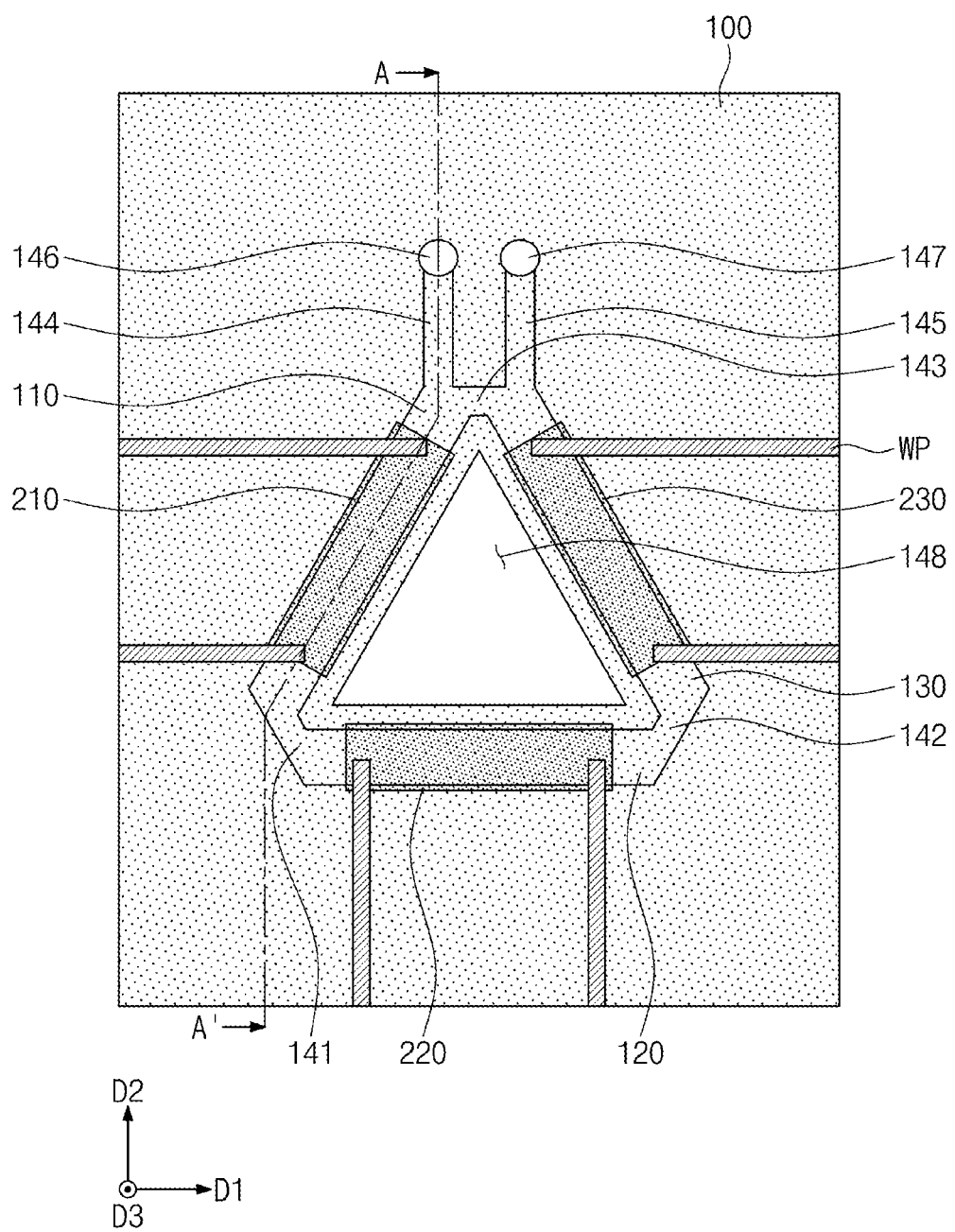
FIG. 1 is a plan view for explaining a device for amplifying and detecting a gene according to an embodiment of the inventive concept.

Embodiments of the inventive concept will be described with reference to the accompanying drawings so as to sufficiently understand constitutions and effects of the inventive concept.

The present invention is not limited to the embodiments disclosed below, but should be implemented in various forms, and various modifications and changes may be made. Rather, these embodiments are provided so that this disclosure will be thorough and complete, and will fully convey the scope of the present invention to those skilled in the art. Further, the present invention is only defined by scopes of claims. In the accompanying drawings, the components are shown enlarged for the sake of convenience of explanation, and the proportions of the components may be exaggerated or reduced for clarity of illustration.

In the following description, the technical terms are used only for explaining a specific exemplary embodiment while not limiting the present invention. Unless terms used in embodiments of the present invention are differently defined, the terms may be construed as meanings that are commonly known to a person skilled in the art.

In this specification, the terms of a singular form may include plural forms unless specifically mentioned. The meaning of 'comprises' and/or 'comprising' specifies a component, a step, an operation and/or an element does not exclude other components, steps, operations and/or elements.

When a layer is referred to herein as being 'on' another layer, it may be formed directly on the top of the other layer or a third layer may be interposed between them.

It will be understood that although the terms first and second are used herein to describe various regions, layers, and the like, these regions and layers should not be limited by these terms. These terms are used only to discriminate one region or layer from another region or layer. Therefore, a portion referred to as a first portion in one embodiment can be referred to as a second portion in another embodiment. An embodiment described and exemplified herein includes a complementary embodiment thereof. Like reference numerals refer to like elements throughout.

Figure 2:
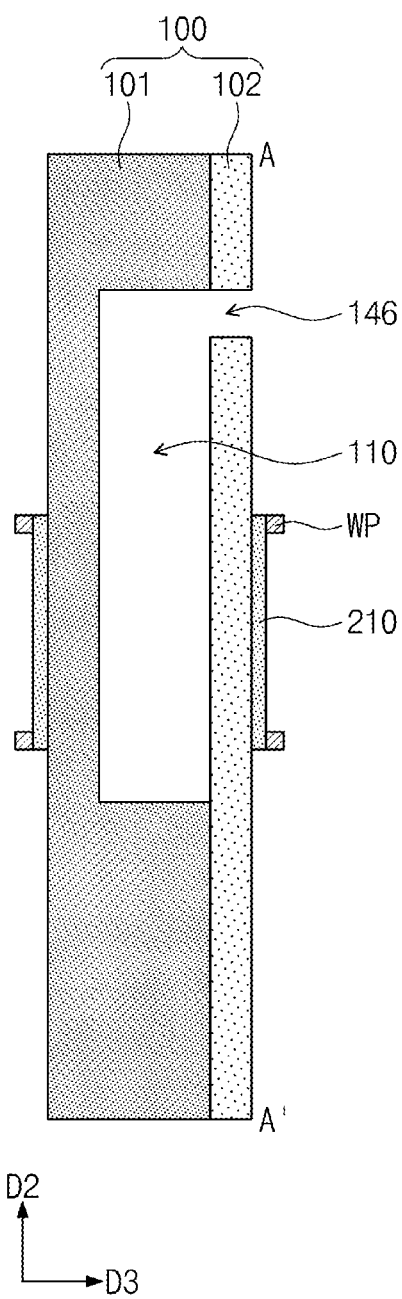
FIG. 2 is a cross-sectional view taken along line A-A' of FIG. 1.

FIG. 1 is a plan view for explaining a device for amplifying and detecting a gene according to an embodiment of the inventive concept. FIG. 2 is a cross-sectional view taken along line A-A' of FIG. 1.

Referring to FIGS. 1 and 2, a device for amplifying and detecting a gene may include a gene amplification chip 100. The gene amplification chip 100 may include a substrate 101 and a cover 102. Each of the substrate 101 and the cover 102 may include a transparent material capable of transmitting light. For example, each of the substrate 101 and the cover 102 may include at least one polymer material of PMMA, PC, PA, PE, PVC, or PVDF, but the material of each of the substrate 101 and the cover 102 is not limited thereto.

The gene amplification chip 100 may include a plurality of channels 110, 120, and 130, a plurality of connection channels 141, 142, and 143, an inflow channel 144, an outflow channel 145, an inlet 146, and an outlet 147.

The gene amplification chip 100 may include a first channel 110, a second channel 120, and a third channel 130, which are provided therein. That is to say, the gene amplification chip 100 may be formed by providing the cover 102 on the substrate 101 in which the plurality of channels 110, 120, and 130 are provided. The first to third channels 110, 120, and 130 may have a triangular loop structure. In a plan view, each of the first to third channels 110, 120, and 130 may correspond to one side in the triangular loop structure.

The gene amplification chip 100 may include a first connection channel 141, a second connection channel 142, and a third connection channel 143, which are provided therein. The first connection channel 141 may connect the first channel 110 to the second channel 120. The second connection channel 142 may connect the second channel 120 to the third channel 130. The third connection channel 143 may connect the third channel 130 to the first channel 110.

Each of widths of the first to third connection channels 141, 142, and 143 may be less than that of each of the first to third channels 110, 120, and 130. The first connection channel 141 may be parallel to the third channel 130. The second connection channel 142 may be parallel to the first channel 110. The third connection channel 143 may be parallel to the second channel 120.

The inlet 146 and the outlet 147 may be provided in the cover 102 for an inflow and outflow of a sample. The inlet 146 may be connected to the first channel 110 through the inflow channel 144. The outlet 147 may be connected to the third channel 130 through the outflow channel 145. The inflow channel 144 and the outflow channel 145 may be parallel to each other.

The gene amplification chip 100 may further include an insulating hole 148 surrounded by the first to third channels 110, 120, and 130 and the first to third connection channels 141, 142, and 143. The insulating hole 148 may be a hole passing through the substrate 101 and the cover 102. The insulating hole 148 may be provided in a center of the gene amplification chip 100. The insulating hole 148 may have the same triangular shape as the triangular loop structure constituted by the first to third channels 110, 120, and 130. The insulating hole 148 may be provided to reduce thermal interference between the first to third channels 110, 120, and 130 and reduce a loss of heat provided from transparent heaters 210, 220, and 230 to be described later.

A first transparent heater 210 may be provided on the first channel 110, a second transparent heater 220 may be provided on the second channel 120, and a third transparent heater 230 may be provided on the third channel 130. The first transparent heater 210 may extend along the first channel 110, the second transparent heater 220 may extend along the second channel 120, and the third transparent heater 230 may extend along the third channel 130. The first to third transparent heaters 210, 220, and 230 may vertically overlap the first to third channels 110, 120, and 130, respectively.

Each of the first to third transparent heaters 210, 220, and 230 may include a transparent material that is capable of transmitting light. As an example, each of the first to third transparent heaters 210, 220, and 230 may include at least one of graphene or indium tin oxide (ITO). Light may be transmitted through the first to third transparent heaters 210, 220, and 230 so as to be provided into the sample. Therefore, after the gene amplification is completed, a degree of the gene amplification may be measured in real time by using a light transmission manner without a separate separation process.

The first to third transparent heaters 210, 220, and 230 may be provided at one side or both sides of the gene amplification chip 100. Referring to FIGS. 1 and 2, the first to third transparent heaters 210, 220, and 230 are respectively disposed on the substrate 101 and the cover 102 (i.e., both sides of) of the gene amplification chip 100, respectively. However, unlike this configuration, the first to third transparent heaters 210, 220, 230 may be provided at only one side of the gene amplification chip 100. For example, the first to third transparent heaters 210, 220, and 230 may be provided only on the cover 102 of the gene amplification chip 100 to vertically respectively overlap the first to third channels 110, 120, and 130.

Electric lines WP may be provided on the first to third transparent heaters 210, 220, and 230, respectively. For example, the electric lines WP may be provided at both ends of the first to third transparent heaters 210, 220, and 230, respectively. Although not shown, the electric lines WP may be connected to a temperature controller (not shown). Each of temperatures of the first to third transparent heaters 210, 220, and 230 may be controlled through the temperature controller (not shown). Each of the temperatures of the first to third transparent heaters 210, 220 and 230 may be constantly maintained by the temperature controller (not shown). The first to third transparent heaters 210, 220, and 230 may generate heat by receiving a voltage from the temperature controller (not shown) through the electric lines WP. The samples may be circulated through the first to third channels 110, 120, and 130 by the temperature controller (not shown). That is, each of the first to third channels 110, 120, and 130 may be a temperature change loop.

The sample may be introduced into the gene amplification chip 100 through the inlet 146 to automatically fill the first to third channels 110, 120, and 130 by gravity. The sample may contain a gene and a fluorescent material. The fluorescent material may be a material of which an emission intensity increases in proportion to the number of genes.

The temperatures of the first to third transparent heaters 210, 220, and 230 may be controlled differently from each other. For example, the first transparent heater 210 may be controlled to a temperature of about 90° C. to about 97° C., the second transparent heater 220 may be controlled to a temperature of about 68° C. to about 74° C., and the third transparent heater 230 may be controlled to a temperature of about 50° C. to 65° C. That is, temperatures of samples filled in the first to third channels 110, 120, and 130 may be controlled differently for each channel. Since the temperatures of the first to third channels 110, 120, and 130 are controlled to be different from each other, a denaturation process inside the first channel 110, an extension process inside the second channel 120, and an annealing process inside the third channel 130 may be performed.

To prevent the sample from leaking, the inlet 146 and the outlet 147 may be sealed, and the temperatures of the first to third transparent heaters 210, 220, and 230 may be controlled. As the sample is heated at a relatively high temperature in the first channel 110 and is heated at a relatively low temperature in the third channel 130, the sample may be circulated in order of the first channel 110, the third channel 130, and the second channel 120. That is to say, the sample may sequentially flow through the first channel 110, the third connection channel 143, the third channel 130, the second connection channel 142, the second channel 120, and the first connection channel 141. That is, the gene amplification reaction may be performed in stages and in sequence while the sample is circulated through the first to third channels 110, 120, and 130 by the first to third transparent heaters 210, 220, and 230.

Figure 3:
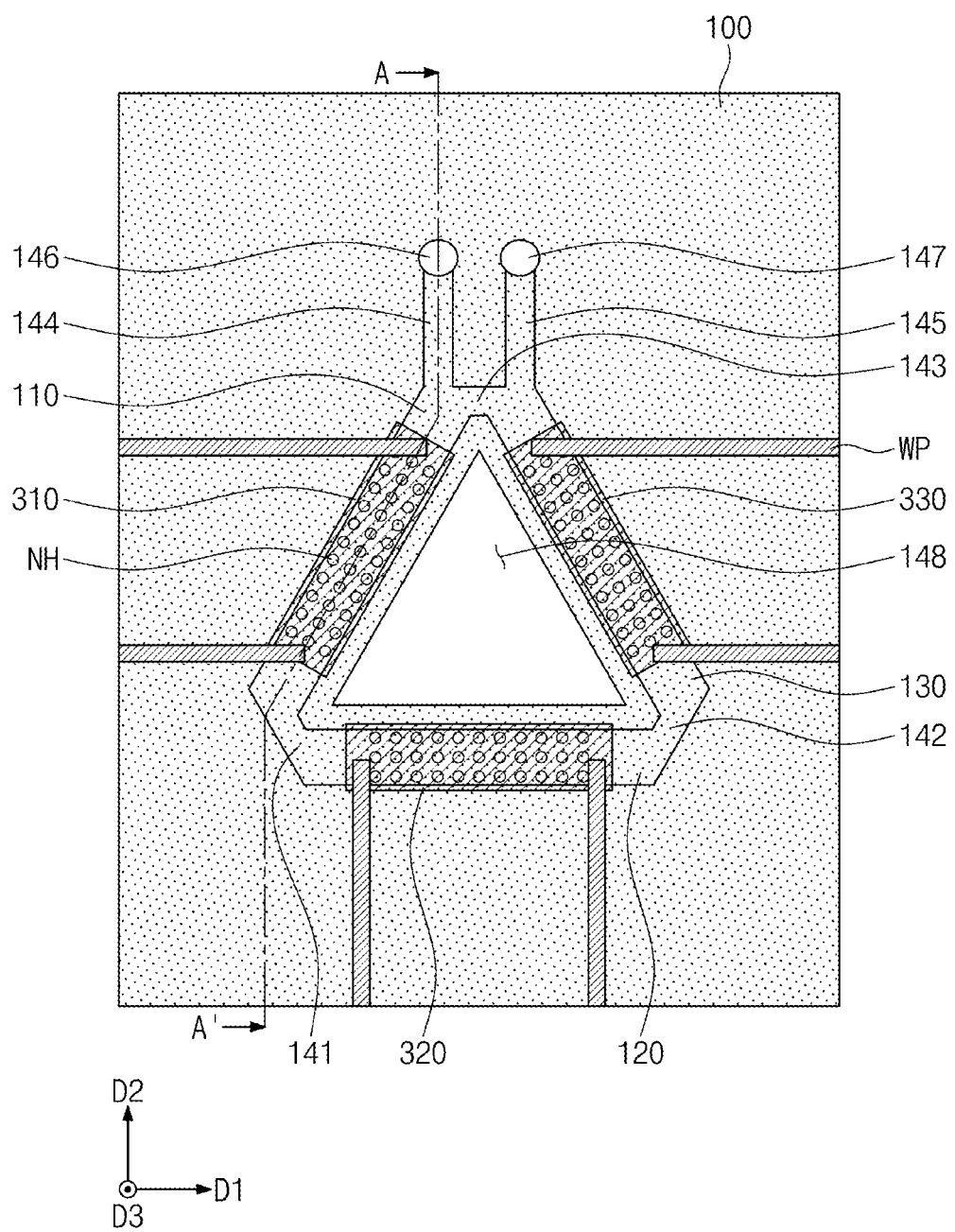
FIG. 3 is a plan view for explaining a device for amplifying and detecting a gene according to another embodiment of the inventive concept.
Figure 4:
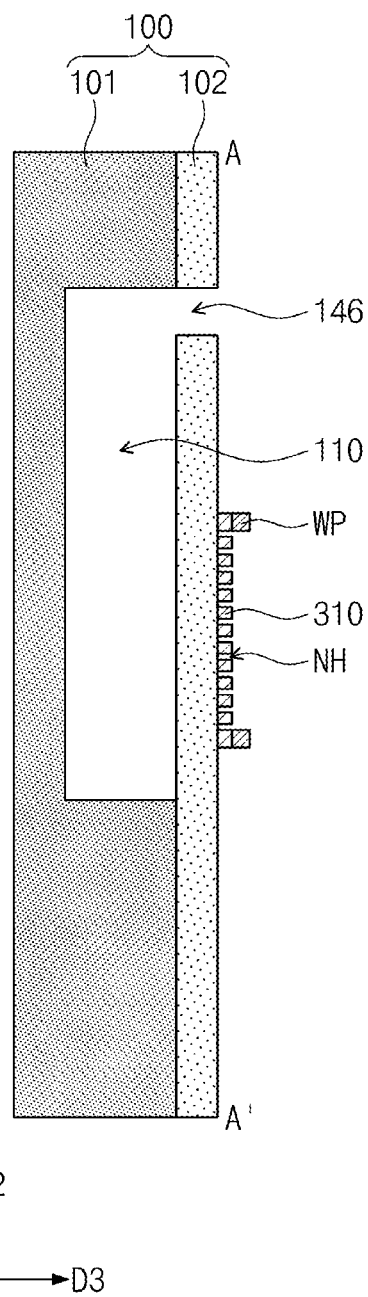
FIG. 4 is a cross-sectional view taken along line A-A' of FIG. 3.

FIG. 3 is a plan view for explaining a device for amplifying and detecting a gene according to another embodiment of the inventive concept. FIG. 4 is a cross-sectional view taken along line A-A' of FIG. 3. In this embodiment, detailed descriptions of technical features that are duplicated with those described with reference to FIGS. 1 and 2 will be omitted, and differences will be described in detail.

Referring to FIGS. 3 and 4, each of first to third transparent heaters 310, 320, and 330 may include a metal thin-film layer. As an example, each of the first to third transparent heaters 310, 320, and 330 may include a metal material such as Cu, Al, or Ag, but the material of each of the first to third transparent heaters 310, 320, and 330 is not limited thereto. The first to third transparent heaters 310, 320, and 330 may be provided on a cover 102 of a gene amplification chip 100. A thickness of the metal thin-film layer may be thin that is enough to transmit light. For example, the thickness of the metal thin-film layer of each of the first to third transparent heaters 310, 320, and 330 may be about 1 μm to about 20 μm.

The metal thin-film layer of each of the first to third transparent heaters 310, 320, 330 may include a plurality of nano holes NH. In the plan view, the nano holes NH may vertically overlap the first to third channels 110, 120, and 130. Outer surfaces of the first to third channels 110, 120, and 130 may be exposed by the nano holes NH. A portion of the cover 102 of the gene amplification chip 100 may be exposed by the nano holes NH.

Intervals between the plurality of nano holes NH may be the same. The metal thin-film layer may include nano-holes NH that are periodically arranged. That is to say, the metal thin-film layer of each of the first to third transparent heaters 310, 320, and 330 may have a photonic crystal structure. Since the metal thin-film layer of each of the first to third transparent heaters 310, 320, and 330 has the photonic crystal structure, light having a specific wavelength may be blocked or transmitted. That is, each of the first to third transparent heaters 310, 320, and 330 may serve as a heater and an optical filter to reduce optical interference between light incident into the gene amplification chip 100 and light emitted from a fluorescent material of the sample.

Each of the intervals between the nano holes NH may have a wavelength in a visible light band. For example, each of the intervals between the nano holes NH may be about 400 nm to about 700 nm. The intervals between the nano holes NH may be adjusted to achieve a wavelength of light to be blocked or transmitted.

Figure 5:
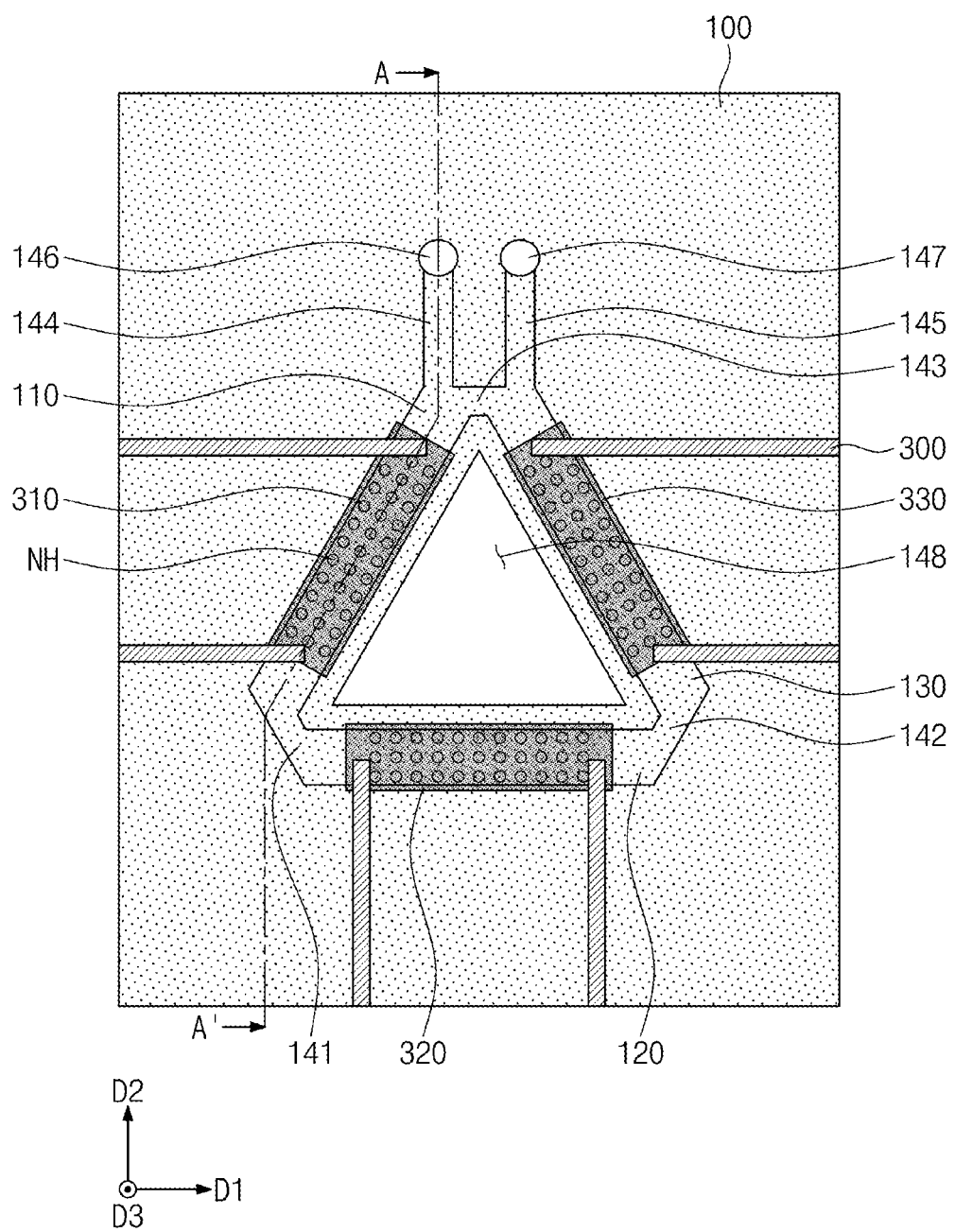
FIG. 5 is a plan view for explaining a device for amplifying and detecting a gene according to another embodiment of the inventive concept.
Figure 6:
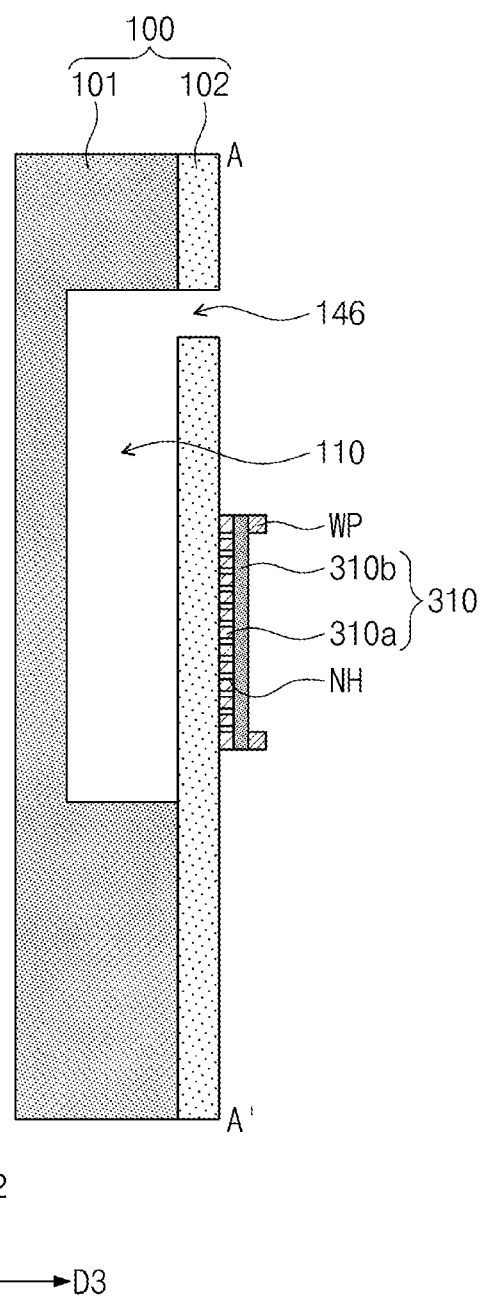
FIG. 6 is a cross-sectional view taken along line A-A' of FIG. 5.

FIG. 5 is a plan view for explaining a device for amplifying and detecting a gene according to another embodiment of the inventive concept. FIG. 6 is a cross-sectional view taken along line A-A' of FIG. 5. In this embodiment, detailed descriptions of technical features that are duplicated with those described with reference to FIGS. 1 and 4 will be omitted, and differences will be described in detail.

Referring to FIGS. 5 and 6, a first transparent heater 310 may include a metal thin-film layer 310a and a graphene layer 310b. Each of a second transparent heater 320 and a third transparent heater 330 may further include a graphene layer.

The graphene layer 310b may be provided on the metal thin-film layer 310a. The graphene layer 310b may be provided on an entire surface of the metal thin-film layer 310a. The graphene layer 310b may vertically overlap nano holes NH of the metal thin-film layer 310a. Electric lines WP may be provided on the graphene layer 310b. The electric lines WP may be provided on both ends of the graphene layer 310b. The graphene layer 310b may be transparent to transmit light.

The graphene layer 310b may function as a kind of pad electrode. Since the metal thin-film layer 310a has a thin thickness, when a voltage is applied through the electric lines WP, a decrease in conductivity may occur. Since the graphene layer 310b is provided on the metal thin-film layer 310a, this limitation may be compensated to more precisely perform a temperature control according to the voltage application. Also, since the graphene layer 310b having excellent thermal efficiency is provided on the metal thin-film layer 310a, a loss of heat applied to the first to third channels 110, 120, and 130 may also be reduced.

Figure 7:
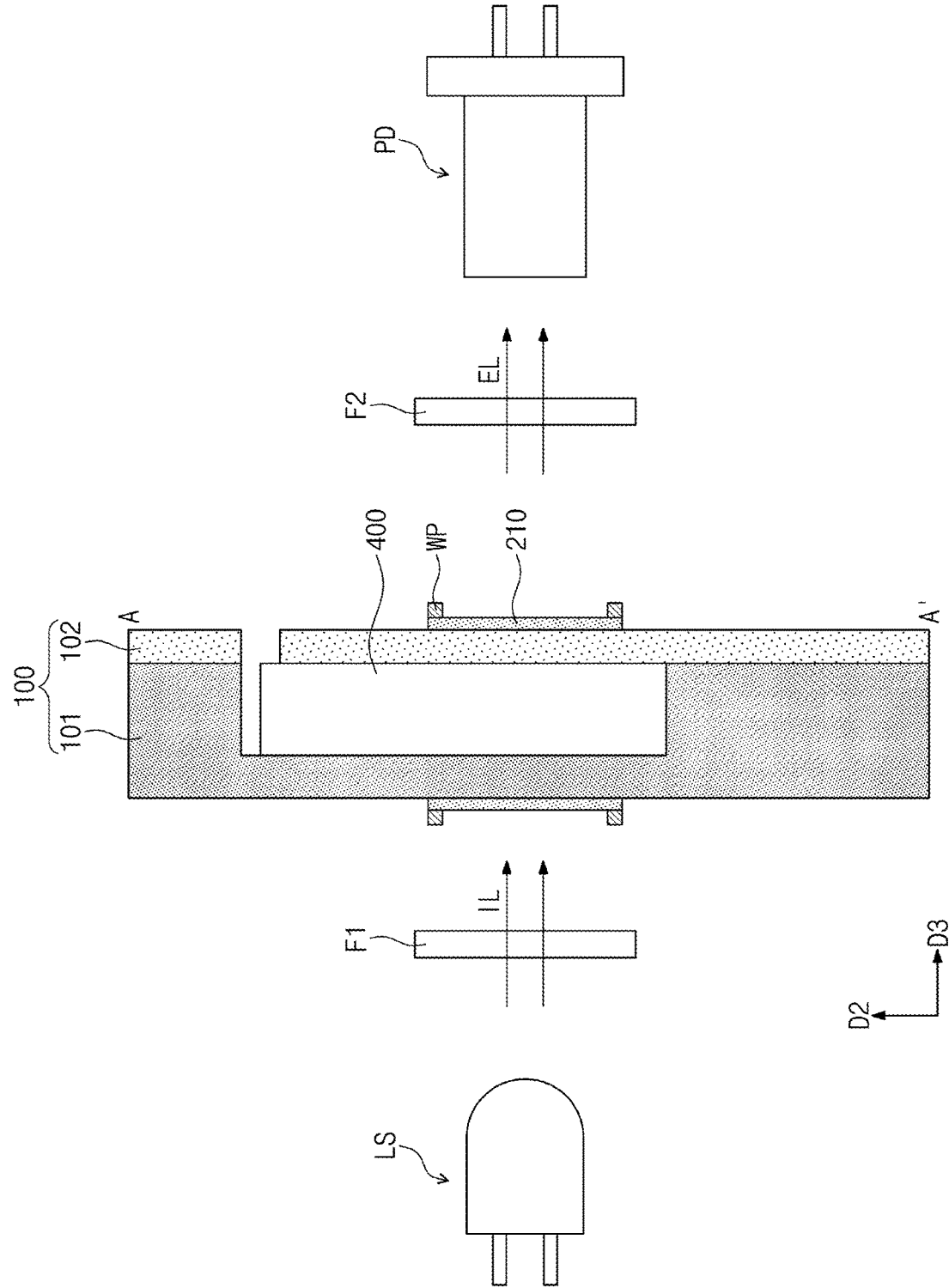
Figure 8:
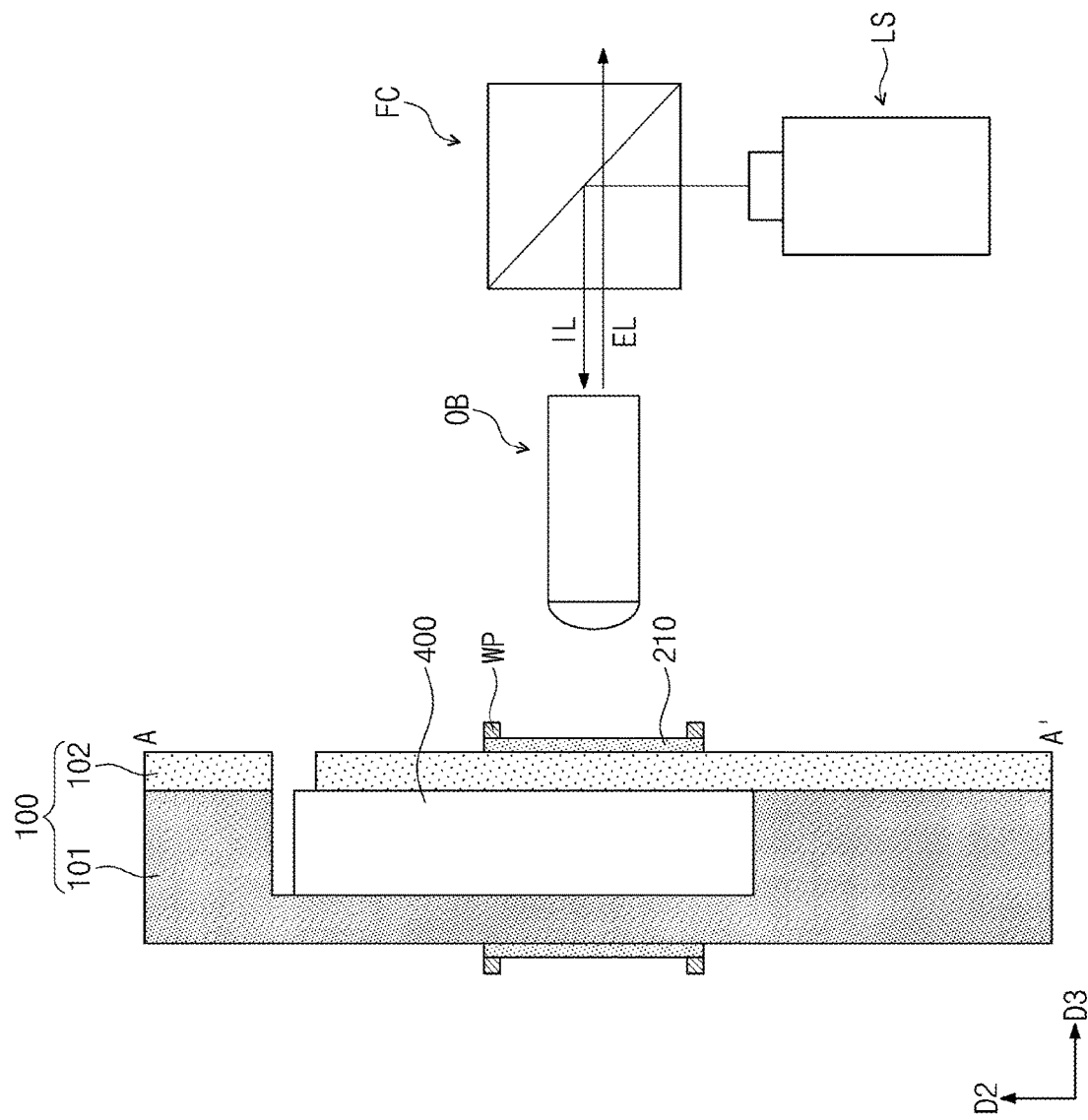

FIGS. 7 to 9 are cross-sectional views for explaining a method for measuring a degree of gene amplification by using the device for amplifying and detecting the gene according to embodiments of the inventive concept.

Referring to FIGS. 7 and 8, a degree of gene amplification may be measured by irradiating light to the device for amplifying and detecting the gene, which is described with reference to FIGS. 1 and 2.

A sample 400 is introduced into first to third channels 110, 120, and 130 provided inside a gene amplification chip 100, and an inlet 146 and an outlet 147 are sealed to prevent the sample 400 from leaking. Thereafter, temperatures of first to third transparent heaters 210, 220, and 230 are controlled to be different from each other to allow the sample 400 to flow along the first to third channels 110, 120, and 130. A gene amplification process is performed by circulating the sample 400 through the first to third channels 110, 120, and 130.

Referring again to FIG. 7, after the gene amplification reaction is completed, incident light IL may be provided to the gene amplification chip 100 from a light source LS. The light source LS may irradiate the incident light IL from one side of the gene amplification chip 100. A fluorescent material inside the sample 400 into which the incident light IL is irradiated may be excited to emit emission light EL. The emission light EL may be emitted to the other side of the gene amplification chip 100.

Here, wavelengths of the incident light IL and the emission light EL may be different from each other. For example, the incident light IL may have a wavelength of about 455 nm to about 495 nm, and the emission light EL may have a wavelength of about 511 nm to about 529 nm. First and second filters F1 and F2 may be disposed to minimize an interference between the incident light IL and the emission light EL. The first filter F1 may be disposed at one side of the gene amplification chip 100, and the second filter F2 may be disposed at the other side of the gene amplification chip 100.

An intensity of the emission light EL emitted from the fluorescent material in the sample 400 may be measured through a photodetector PD. The photodetector PD may be disposed at the other side of the gene amplification chip 100. The degree of the gene amplification may be measured through the intensity of the emission light EL, which is measured from the photodetector PD.

Referring again to FIG. 8, the incident light IL irradiated from the light source LS may be sequentially transmitted through a filter cube FC and an objective lens OB and then be provided to the sample 400 in the gene amplification chip 100. The emission light EL emitted by the fluorescent material inside the sample 400 may be sequentially transmitted through the objective lens OB and the filter cube FC. The light source LS, the objective lens OB, and the filter cube FC may be disposed at one side of the gene amplification chip 100.

Here, wavelengths of the incident light IL and the emission light EL may be different from each other. For example, the incident light IL may be blue light, and the emission light EL may be red light. The filter cube FC for minimizing the interference between the incident light IL and the emission light EL may be provided.

Since the transparent heaters through which light is transmitted are provided on the gene amplification chip 100, results of the gene amplification may be checked in real time by using a light transmission method in which light is simply irradiated without a separate separation process.

Referring to FIG. 9, the degree of the gene amplification may be measured through the device for amplifying and detecting the gene, which is described with reference to FIGS. 3 and 4.

The light source LS is disposed at one side of the gene amplification chip 100, and the incident light IL irradiated from the light source LS may be provided to the sample 400. The photodetector PD may be disposed at the other side of the gene amplification chip 100 to measure the intensity of the emission light EL emitted from the fluorescent material inside the sample 400. For example, the incident light IL may have a wavelength of about 455 nm to about 495 nm, and the emission light EL may have a wavelength of about 511 nm to about 529 nm.

Since each of the transparent heaters on the gene amplification chip 100 includes a metal thin-film layer of a photonic crystal structure, unlike FIGS. 7 and 8, the intensity of the emission light EL may be measured without providing a filter that prevents the optical interference between the incident light IL and the emission light EL. That is to say, the transparent heaters block a wavelength band of the incident light IL and may serve as a filter that transmits a wavelength band of the emission light EL emitted from the fluorescent material inside the sample 400.

Since the device and method for amplifying and detecting a gene according to the embodiment of the inventive concept uses the transparent heater, the temperature loss may be minimized, and after the gene amplification is completed, the degree of the gene amplification may be measured in real time.

The object of the present invention is not limited to the aforesaid, but other objects not described herein will be clearly understood by those skilled in the art from descriptions below.

Although the embodiment of the inventive concept is described with reference to the accompanying drawings, those with ordinary skill in the technical field of the inventive concept pertains will be understood that the present disclosure can be carried out in other specific forms without changing the technical idea or essential features. Therefore, the above-disclosed embodiments are to be considered illustrative and not restrictive.

What is claimed is:

1. A device for amplifying and detecting a gene, the device comprising:
   a gene amplification chip comprising channels through which a sample flows; and
   transparent heaters provided on the gene amplification chip,
   wherein the channels comprise a first channel, a second channel, and a third channel, and the first to third channels have a triangular loop structure,
   the transparent heaters comprise a first transparent heater, a second transparent heater, and a third transparent heater, which are respectively provided on the first to third channels,
   each of the first to third transparent heaters comprises a metal thin-film layer and a graphene layer,
   the metal thin-film layer is disposed between the graphene layer and the gene amplification chip, and
   the metal thin-film layer comprises a plurality of nano holes.

2. The device of claim 1, wherein each of the first to third transparent heaters comprises at least one of graphene or ITO.

3. The device of claim 1, wherein the first transparent heater extends along the first channel, the second transparent heater extends along the second channel, and the third transparent heater extends along the third channel.

4. The device of claim 1, wherein the gene amplification chip further comprises an insulating hole surrounded by the first to third channels.

5. The device of claim 1, wherein temperatures of the first transparent heater, the second transparent heater, and the third transparent heater are controlled to be different from each other.

6. The device of claim 1, further comprising:
   an inlet through which the sample is introduced;
   connection channels configured to connect the first to third channels to each other; and
   an outlet through which the sample is discharged.

7. The device of claim 1, wherein intervals between the nano holes of the metal thin-film layer are the same.

\* \* \* \* \*